United States Patent [19]
Zeimer

[11] Patent Number: 5,943,116
[45] Date of Patent: Aug. 24, 1999

[54] SYSTEM FOR IMAGING AN OCULAR FUNDUS SEMI-AUTOMATICALLY AT HIGH RESOLUTION AND WIDE FIELD

[75] Inventor: Ran Zeimer, Reisterstown, Md.

[73] Assignee: Johns Hopkins University, Baltimore, Md.

[21] Appl. No.: 09/052,117

[22] Filed: Mar. 31, 1998

Related U.S. Application Data

[60] Provisional application No. 60/041,783, Apr. 1, 1997.

[51] Int. Cl.[6] .................................................. A61B 3/00
[52] U.S. Cl. ............................................................ 351/221
[58] Field of Search ................................... 351/200, 205, 351/206, 207, 208, 211, 221, 246

[56] References Cited

U.S. PATENT DOCUMENTS

| | | |
|---|---|---|
| 3,914,032 | 10/1975 | Takano et al. . |
| 3,936,844 | 2/1976 | Matsumura . |
| 4,068,932 | 1/1978 | Ohta et al. . |
| 4,132,466 | 1/1979 | Matsumura . |
| 4,196,979 | 4/1980 | Kohayakawa et al. . |
| 4,238,142 | 12/1980 | Richards et al. . |
| 4,248,506 | 2/1981 | Takahashi . |
| 4,249,802 | 2/1981 | Muchel et al. . |
| 4,266,861 | 5/1981 | Sawa . |

(List continued on next page.)

OTHER PUBLICATIONS

Johnathan C. Javitt et al., "Detecting and Treating Retinopathy in Patients with Type I Diabetes Mellitus", *Ophthamology*, vol. 98, No. 10, Oct., 1991, pp. 1565–1574.

Daniel E. Singer et al., "Screening for Diabetic Retinopathy", *Annals of Internal Medicine*, vol. 116, No. 8, Apr. 15, 1992, pp. 660–670.

"Screening Guidelines for Diabetic Retinopathy", *Ophthalmology*, vol. 99, No. 10, Oct., 1992, pp. 1626–1628.

David R. Lairson, PHD et al., "Cost–Effectiveness of Alternative Methods for Diabetic Retinopathy Screening", *Diabetes Care*, vol. 15, No. 10, Oct., 1992, pp. 1369–1377.

Frederick L. Ferris III, MD, "Diabetic Retinopathy", *Diabetes Care*, vol. 16, Supplement 1, Jan., 1993, pp. 322–325.

Ross J. Brechner, MD, MS, MPH et al., "Ophthalmic Examination Among Adults With Diagnosed Diabetes Mellitus", *JAMA*, vol. 270, No. 14, Oct. 13, 1993, pp. 1714–1718.

*Primary Examiner*—George Manuel
*Attorney, Agent, or Firm*—Roylance,Abrams,Berdo & Goodman, L.L.P.

[57] ABSTRACT

A system for obtaining images of the fundus of an eye includes an illumination device which directs a light beam onto a portion of the fundus of the eye, and a video camera which records the portion of the light reflected from the fundus of the eye. The pupil of the eye is automatically centered and brought into focus, and the fundus of the eye is then automatically brought into focus. A plurality of target images are presented at different locations in space so that the eye will move when focusing on these different locations. As the eye moves, different areas of the fundus are illuminated, and images of these different areas of the fundus are recorded by the video camera. The plurality of images from the different areas of the fundus are then automatically arranged by a computer in a mosaic image representative of a section of the fundus including the plurality of areas. Data representative of the mosaic image is transmitted to a remote site for analysis. Additionally, the system can perform visual acuity and perimetry testing on the eye whose fundus is being imaged.

35 Claims, 8 Drawing Sheets

U.S. PATENT DOCUMENTS

| | | |
|---|---|---|
| 4,423,932 | 1/1984 | Takahashi . |
| 4,439,023 | 3/1984 | Iba et al. . |
| 4,449,798 | 5/1984 | Nohda . |
| 4,558,932 | 12/1985 | Numokawa . |
| 4,679,919 | 7/1987 | Itoh et al. . |
| 4,704,018 | 11/1987 | Takhashi . |
| 4,715,703 | 12/1987 | Cornsweet et al. ............... 351/206 |
| 4,717,952 | 1/1988 | Kohayakawa et al. ............ 351/206 |
| 4,738,521 | 4/1988 | Volk . |
| 4,755,044 | 7/1988 | Thorn . |
| 4,773,749 | 9/1988 | Ohtomo et al. . |
| 4,797,942 | 1/1989 | Burt . |
| 4,991,584 | 2/1991 | Kobayashi et al. . |
| 5,125,730 | 6/1992 | Taylor et al. . |
| 5,140,352 | 8/1992 | Moore et al. . |
| 5,297,034 | 3/1994 | Weinstein . |
| 5,333,017 | 7/1994 | Volk . |
| 5,347,331 | 9/1994 | Isogai et al. . |
| 5,465,147 | 11/1995 | Swanson . |
| 5,502,520 | 3/1996 | Cibis et al. . |
| 5,504,542 | 4/1996 | Hino et al. ........................ 351/206 |
| 5,508,760 | 4/1996 | Kobayashi et al. . |
| 5,543,865 | 8/1996 | Nanjo . |
| 5,568,208 | 10/1996 | Van de Velde . |

SYSTEM FOR IMAGING AN OCULAR FUNDUS SEMI-AUTOMATICALLY AT HIGH RESOLUTION AND WIDE FIELD

RELATED APPLICATION

This application claims the benefit of U.S. Provisional Application Ser. No. 60/041,783, filed Apr. 1, 1997.

BACKGROUND OF THE INVENTION

1. Field of the Invention:

The present invention relates to an apparatus and method for photographing the fundus of an eye. More particularly, the present invention relates to an apparatus and corresponding method which obtains images of a plurality of different portions of the fundus of the eye, and arranges those images to create a mosaic image of a section of the fundus of the eye comprising the plurality of different portions.

2. Description of the Related Art

In industrial countries, the most common eye diseases, aside from cataract, are diabetic retinopathy, glaucoma and age macular degeneration. Although these diseases can lead to severe losses in vision, if treated at the appropriate stage, the risk of vision loss is reduced significantly.

In order to detect the onset of treatable disease, persons at risk should be examined by an eye care specialist on a regular schedule. Unfortunately, only a portion of these persons is examined routinely. For example, on average, half of all diabetic patients do not visit an ophthalmologist as recommended. This lack of monitoring, not related to the availability of care, leads to an unnecessary elevated incidence of vision loss accompanied by low quality of life, high cost of health management, and loss of productivity of persons affected and their custodians. There is thus an effort to find available means to screen for common eye diseases.

Since those at risk for such eye diseases generally make regular visits to primary care physicians, it is advantageous to perform at the physicians' offices. However, at present, there are no adequate devices to perform the screening. The devices must be easy to use by office staff, rapid, sensitive, as accurate as possible and, most importantly, affordable.

Photography has been used for aiding in the diagnosis of common eye disorders, and is often considered superior to ophthalmic examinations for the detection of a number of diseases and diagnosis of numerous eye disorders such as diabetic retinopathy and glaucoma. For diseases like diabetic retinopathy, photographs allow the eye care specialist to detect the presence of pathologies such as abnormal blood vessels, deposits of components, such as lipids that have leaked from the vessels, and edema. For detecting glaucoma, the photographs are useful for examining the optic disc and its vicinity for loss of nerve fibers.

In addition, diagnostic methods are used to assess vision. Typically, losses are detected by psychophysical tests which evaluate the response of the subject to visual stimuli.

Unfortunately, these proven methods at present are only available to eye care specialists. A need therefore exists for a system which enables these tests to be performed in a manner that fits the practical needs of a plurality of screening environments, such as primary care physicians offices, optometrists offices, large places of employment place and mobile units.

In order to screen for common eye diseases efficiently, the imaging system must provide images with a relatively large field of view (e.g. about 50°) measured as the conical angle originating at the pupil and extending towards the area on the retina being imaged. Such a field of view is sufficient for reliable detection of common diseases such as diabetic retinopathy, glaucoma and age related macular degeneration. The imaging system should also provide a resolution of 60 pixels or more per degree. Conventional fundus photographic images are currently acquired on film with a resolution adequate for diagnosis as long as the field of view is 30° or less. The resolution of conventional photographs on film is about 60 pixels per degree. Therefore, a total of approximately 1800 pixels (measured diagonally) is achieved (i.e., 30°×60 pixels per degree=1800 pixels). For the desired field of 50°, a total of 3000 pixels measured diagonally would be achieved.

Stereo imaging with a constant stereo angle is also desirable in such an imaging system. The detection of macular edema, a common cause of vision loss, is routinely based on the examination of stereo pairs of fundus images to detect retinal thickening. The stereo angle is the angle between the two imaging paths of the two images. By viewing these images, each with a different eye, the examiner obtains a sensation of depth. This stereo effect is enhanced by increasing the stereo angle. Therefore, to obtain a stereo sensation that can be used to compare images, the stereo angle should be constant.

The system should also allow for efficient operation by non-ophthalmic staff. The most efficient method to screen for common eye diseases can be achieved by examining the eye during routine visits to primary care physicians, as opposed to requiring visits to an ophthalmic specialist. Thus, the camera should be specifically designed for operation by nonophthalmic staff. The system should further provide cost efficient screening. For screening to be incorporated in routine health care delivery, the cost needs to be modest and commensurate with the financial and medical benefit.

Additionally, the system should be capable of performing imaging without pharmacological pupil dilation. Conventional fundus photography requires pharmacological pupil dilation by use of a topical instillation of a drug that dilates the pupil to prevent it from constricting upon exposure to the light necessary for photography. Imaging without the installation of a drug makes the process easier and quicker. This requirement is not crucial because pharmacological pupil dilation is a common procedure used for thorough eye exams.

Conventional fundus cameras yield the desired resolution for a field of view of only up to about 30°, which is much smaller than the preferred 50° field of view. To cover the desired larger area, the photographer is required to manually aim the camera to multiple adjacent regions and obtain multiple photographs. Stereo images are acquired by obtaining one photograph through the right side of the pupil, then manually moving the camera to take a second image through the left side of the pupil. This procedure yields images with an unknown stereo base and thus an unknown and varying perception of thickness and depth. In order to yield images adequate for diagnostic purposes, conventional fundus imaging and stereo imaging necessitate operation by a trained ophthalmic photographer. Pharmacological dilation is also typically needed. Finally, the cost and the inconvenience of film make these cameras inadequate for screening.

Digital cameras that yield images with 2000 pixels in diameter have been optically coupled to conventional fundus cameras and have yielded 30° field images with adequate resolution. As the digital cameras record the image electronically and store them in memory, there is no need for film. However, such systems are inadequate because they share the same drawbacks mentioned for the conventional camera to which they are coupled. In addition, the elevated price of these digital cameras adds to the cost of the screening, rendering it unattractive in locations with a small volume of target individuals.

Some fundus cameras provide images or markers to assist the operator in the alignment of the pupil. One known camera provides auto focusing. Other cameras have been designed to obtain images without pharmacological dilation. Still other cameras have been specifically designed to obtain simultaneous stereo pairs, but their resolution is reduced because each frame on the film is shared by the two images that form the stereo pair. None of these cameras provide a large enough photographic field at the required resolution.

Furthermore, as mentioned above, psychophysical tests, namely, tests performed to assess the mental perceptions of physical stimuli, are important in ophthalmology. Most of these tests are intended to detect pathology in the retina or the neural pathway. Visual acuity and visual field tests (perimetry) are an example. Visual acuity assesses central vision, namely, the ability of the subject to perceive small objects, and perimetry testing is aimed at detecting losses of vision mostly in the more peripheral region of the fundus. However, when faced with a response below that of normal subjects, the vision care specialist may have difficulty in determining whether the reduced response is due to optical obstacles in the media or caused by retinal and neuroretinal abnormalities. The management of the patients depends on this differential diagnosis. For example, a reduced visual field response can be due to insufficient dilation of the pupil or opacities in the lens. A poor visual acuity could be caused by opacities and optical aberrations. Finally, in tests such as perimetry, it is difficult to assess the location on the fundus that is responsible for the abnormal response.

Accordingly, a continuing need exists for a system which is capable of obtaining a photographic image of the fundus with the desired resolution and field of view, as well as a system which is capable of measuring visual acuity and visual field.

SUMMARY OF THE INVENTION

An object of the present invention is to provide a system that is capable of obtaining a photographic image of the fundus of an eye having a desired resolution with a desired field of view of, for example, 50° or more.

A further object of the invention is to provide a fundus imaging system which is also capable of performing visual acuity and visual field tests of the eye whose fundus image is being obtained.

A further object of the invention is to provide a system for obtaining an image of a fundus of the eye having desired resolution and field, and transmitting that image to a remote site for analysis.

These and other objects of the present invention are substantially achieved by providing a system which includes an optical head used at the site of screening (e.g., typically at the office of the primary care physician) to digitally acquire images and transmit them via electronic lines to a remote reading center module. The optical head utilizes a relatively inexpensive, conventional video camera to record a fundus image across a small field. A plurality of such images are acquired at different locations on the fundus and, later, a high-field high-resolution image is automatically constructed by generating a mosaic of these images.

Moreover, due to the use of high rate video imaging, stereo pairs can be acquired automatically with a delay well below the time for eye movements and with a constant stereo angle.

To cover the larger than 30° field, and preferably 50° or larger field, at a resolution of 60 pixels per degree, an image equivalent to 3000 pixels in diameter is required. Conventional video cameras can yield images of 930 pixels or more in diameter. In accordance with the present invention, the necessary area is covered with a mosaic of preferably 9 to 16 images. The invention provides a means to efficiently acquire such images under the operation of relatively untrained personnel.

Furthermore, once the eye has been imaged, the plane of the video camera sensor is optimally conjugated to the fundus. By replacing the camera with a plurality of graphic objects, psychophysical tests can be performed whereby the subject responds to the presentation of the objects. One such set of objects consist of letters or symbols used to test visual acuity. Another set can consist of gratings varying temporally and spatially and presented to the peripheral retina as used for visual field testing. The invention includes means to monitor the fixation of the subject and to derive the location of the stimulus on the fundus.

At the reading center a computerized module processes, under the supervision of trained staff, the images and generates a wide-field composite image, and stereo images if necessary. Moreover, the computer module analyzes the results of the psychophysical tests and determines the probability of pathology.

BRIEF DESCRIPTION OF THE DRAWINGS

Referring now to the drawings which form a part of the original disclosure.

DETAILED DESCRIPTION OF THE PREFERRED EMBODIMENTS

Figure 1:
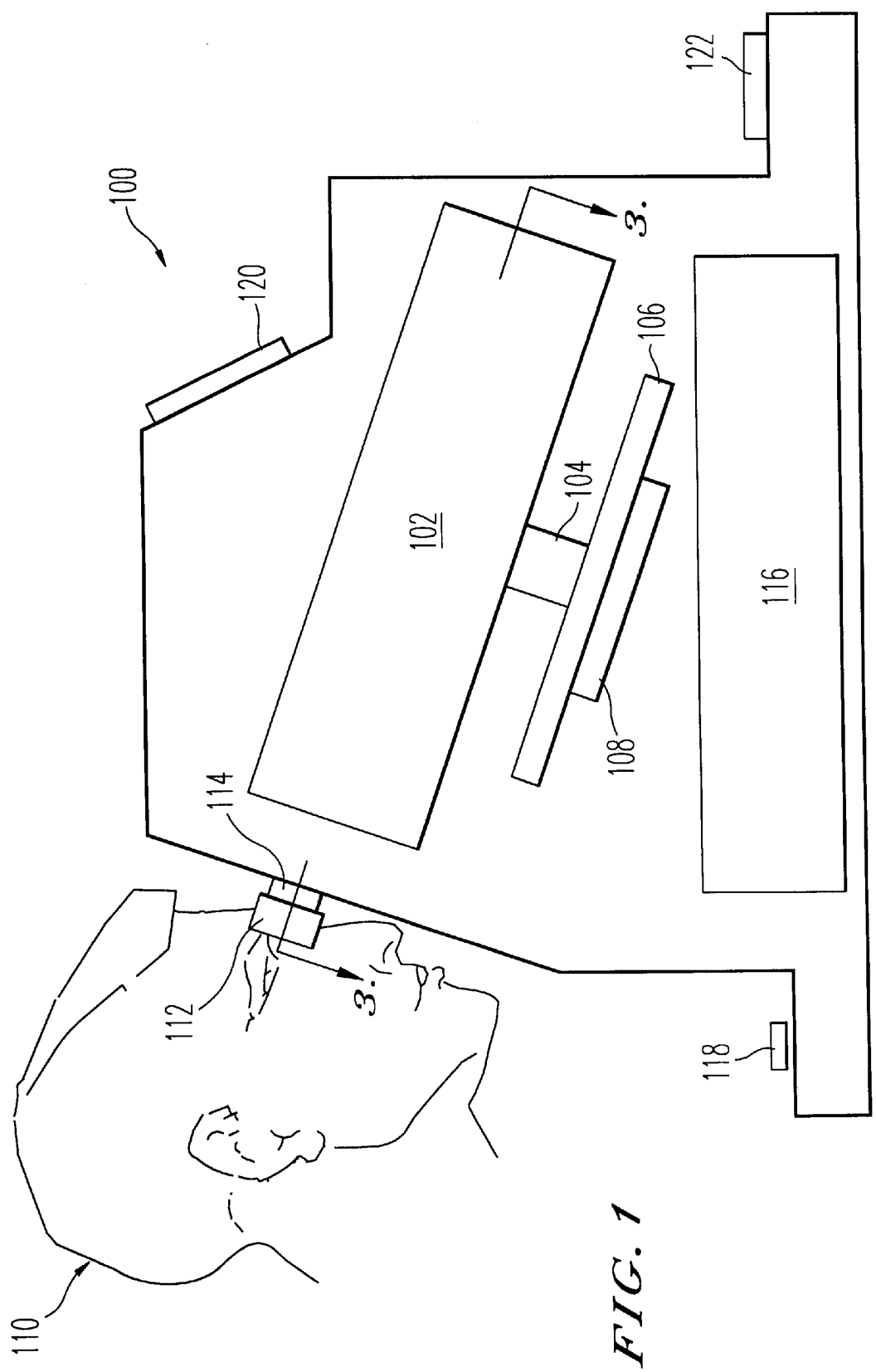
FIG. 1 is a schematic view of an example of an imaging system according to an embodiment of the present invention, which is employed as a data acquisition system for obtaining an image to be transmitted to a remote data analysis center.
Figure 3:
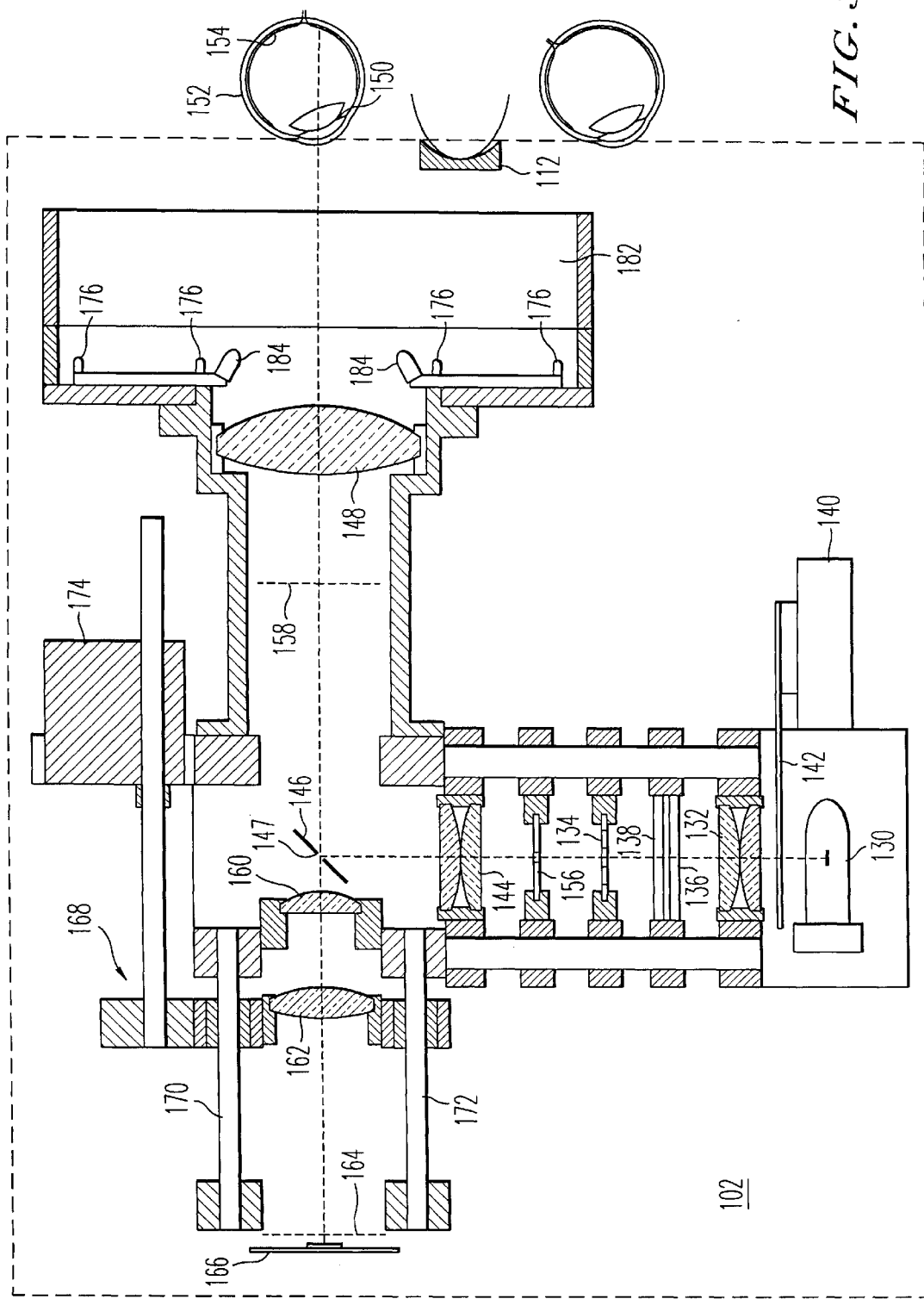
FIG. 3 is a schematic inverted cross-sectional view of the system shown in FIG. 1 as taken along lines 3—3 in FIG. 1 and illustrating, in particular, the optical head.

An example of an imaging system 100 according to an embodiment of the present invention is shown schematically in FIGS. 1 and 3. The system includes an imaging head or subassembly 102 mounted on an XYZ motorized and computer-controlled stage assembly comprising components 104, 106 and 108. The components 104, 106, and 108 are responsible for movement in the X, Y, and Z directions, respectively. As described in more detail below, during operation, the subject 110 leans the bridge of the nose against a nose pad 112 and views one of the target diodes (see FIGS. 3 and 4) inside the imaging subsystem 102 used for fixation. A switch 114 is activated upon placement of the nose against nose pad 112, thus indicating to the computer 116 that the nose is properly positioned.

The electronics and computer 116 that control the entire system are placed under the imaging sub-assembly 102. The subject is provided access to a button 118 and the operator is provided access to a monitor 120 and a touch pad 122 that controls the position of a cursor on the monitor 45. The purpose of these items is described below.

Figure 2:
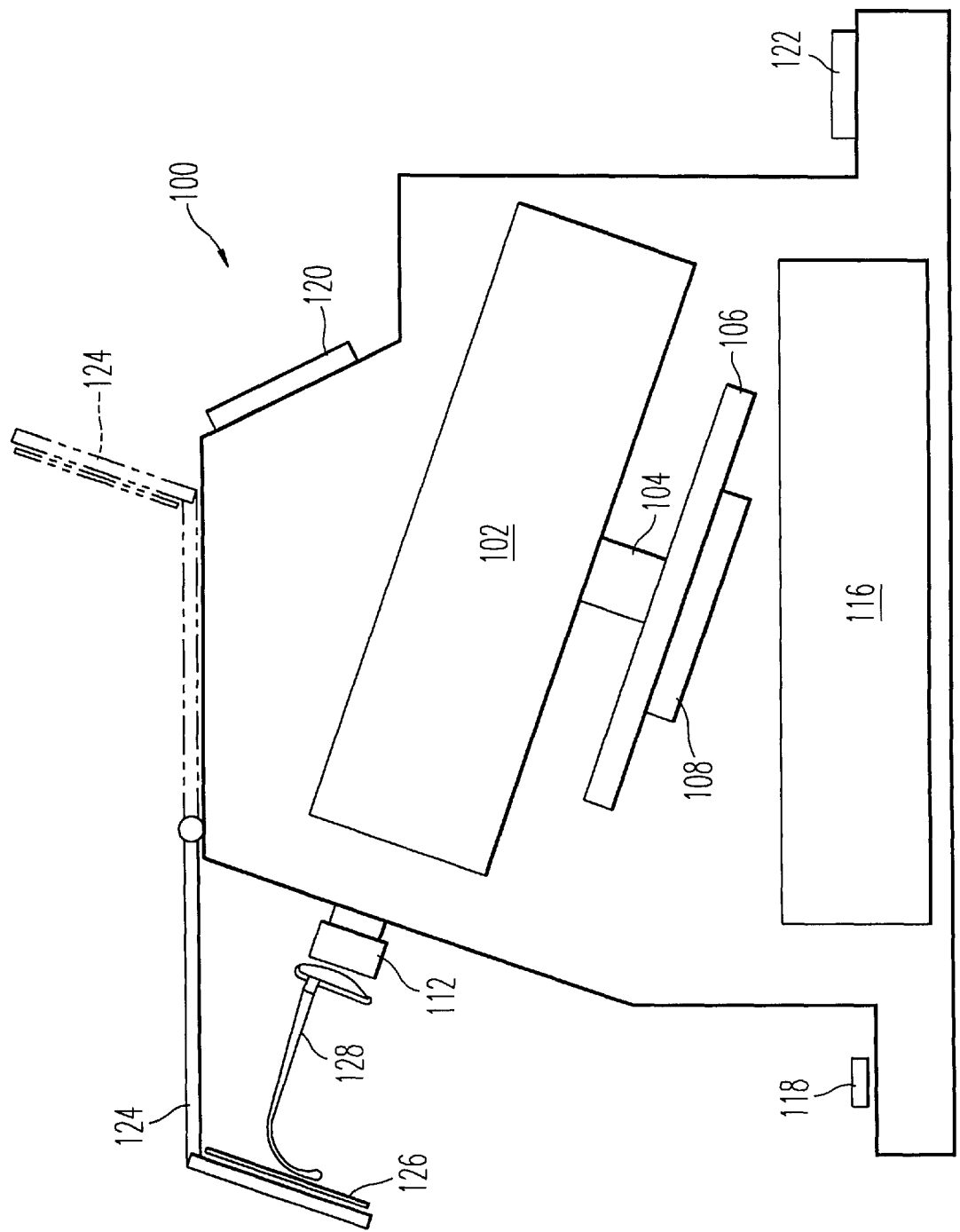
FIG. 2 is a schematic view of the imaging system as shown in FIG. 1, further including a device for performing a refractive error estimation procedure.

As shown in FIG. 2, a holder 124 is able to flip from a resting position (shown by the dotted lines) to a preset distance from the nose pad 112. The subject's chart 126 or any other standardized identification sheet, is placed on an inner surface of the holder 124 when the holder 124 is at the preset distance from nose pad 112. To estimate the subject's refractive error and to set the initial position of focusing lens (See FIGS. 3 and 4) for a particular eye, the subject's spectacles 128 are held by a spectacle holder (not shown) in front of the camera in the manner shown. The instrument performs a focusing routine described in detail below and determines the location of the lens needed to focus the image of the chart 126. This position of lens is stored by the computer 116 and taken into account when automatic focusing of the fundus image is performed.

Figure 4:
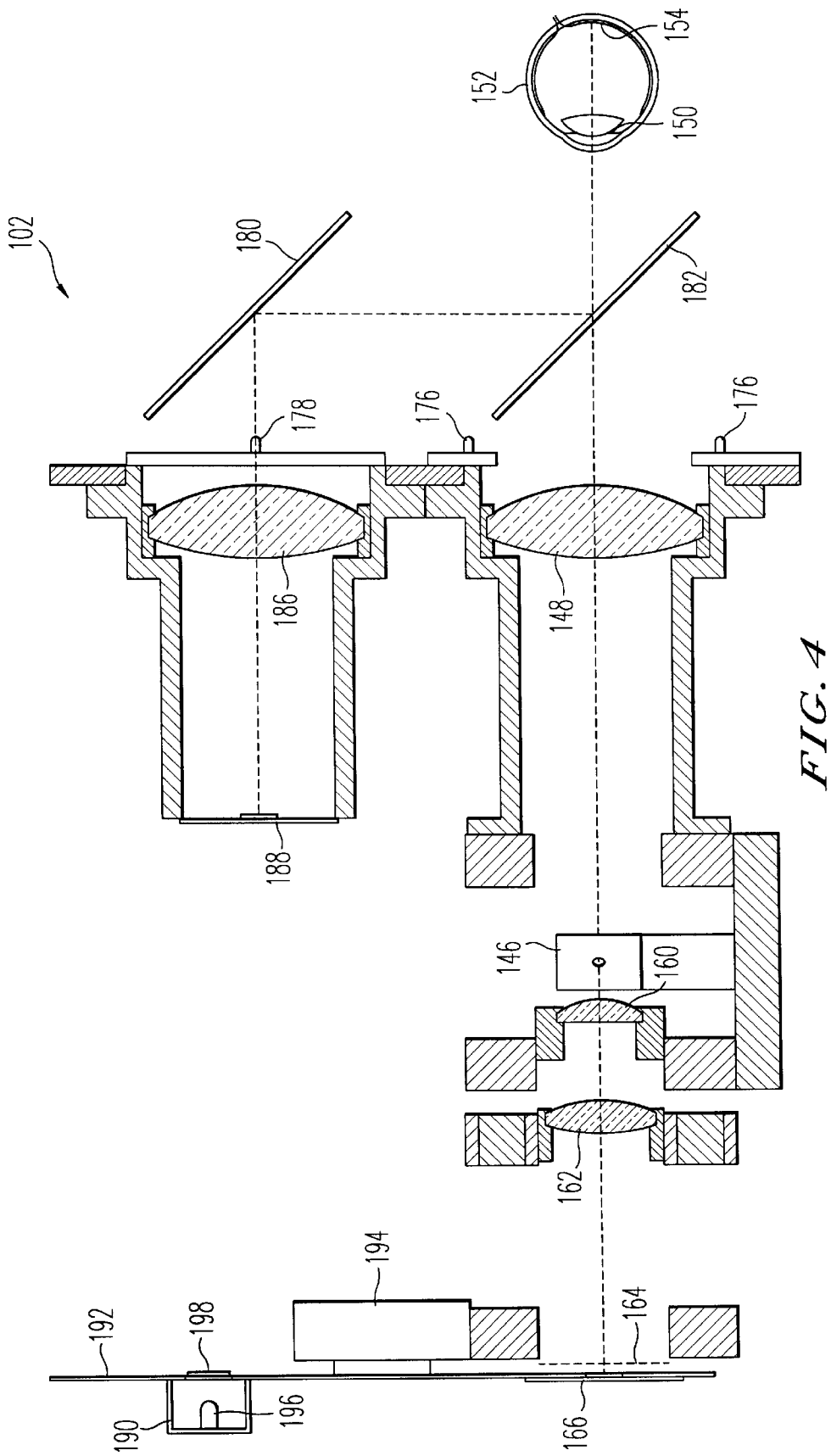
FIG. 4 is a schematic inverted cross-sectional view of the system shown in FIG. 1 as taken in a direction perpendicular to lines 3—3 in FIG. 1 and illustrating, in particular, the optical head.

FIG. 3 is a schematic inverted cross-sectional view of the optical head or subsystem 102, as taken along lines 3—3 in FIG. 1, in relation to a nose pad 112 and an eye being examined. FIG. 4 on the other hand, is a schematic inverted cross-sectional view of the optical head or subsystem 102 as taken in a direction perpendicular to lines 3—3 in FIG. 1. As shown in FIGS. 3 and 4, and as described in more detail below, the optical head or subsystem 102 includes a halogen bulb 130 which generate light that is focused by lenses 132 on a doughnut shaped aperture 134. Infra-red light is eliminated by a filter 136, and the visible spectrum is limited by filter 138 to green light (around 540 nm). A computer controlled solenoid 140 turns the light beam on and off by moving a blade 142 to act as a shutter.

The aperture is imaged and focused by lenses 144 on a mirror 146 provided with a central opening 148. The light from bulb 130 is reflected by mirror 146 and aperture 134 is imaged by lens 148 on the pupil 150 of the eye 152. From the pupil, the beam expands and illuminates the fundus 154. The amount of illumination light reflected by the surfaces of lens 148 is minimized by blocking the rays that impinges on the central portion of lens 148. This is achieved by a small mask 156 that is imaged on lens 148. If necessary, mask 156 consists of two masks separated by a small distance such that each mask is imaged on the front and back surfaces of lens 148 respectively.

The image of the fundus 154 is thus created on a conjugate plane 158. Lenses 160 and 162 together transfer the image at the conjugate plane 158 to conjugate plane 164. A sensing area of a video camera 166 is placed at this plane. Lens 162 is moved to compensate for the spherical refractive error of the eye and thus to optimize the focus on the sensing area of video camera 166. The motion of focusing lens 162 is achieved by mounting it on a holder 168 that slides on two rods 170 and 172. The motion of the holder 168 is generated by a computer controlled linear actuator 174 linked to holder 168. The green and infrared free light emanating from the illumination arm is used to illuminate the fundus 154 and image it on plane 164 and video camera 166. The use of green light is advantageous for imaging blood vessels and vascular pathologies because it is strongly absorbed by blood and thereby provides optimal contrast. The output of camera 166 is fed into an image acquisition board located in computer 116 (FIGS. 1 and 2).

To obtain images at different locations on the fundus, the eye is directed to different orientations by presenting a plurality of lights emitting diode targets 176 and 178 (FIG. 4) that are turned on in a preset order by computer control. Diodes 176 provide fixation for all the locations except the central (foveal) one. The central fixation is provided by diode 178 that is viewed by the observer via mirrors 180 and 182. In a preferred embodiment, an array of nine (3×3), twelve (3×4) or sixteen (4×4) diode targets 176 and 178 are used for each eye. In FIGS. 3 and 4 an array of (4×3) diodes are included for illustration, but only two diodes are shown in FIG. 4.

The operation of the system will now be described in view of FIGS. 1–4.

The operator inputs an identification number for the patient by controlling, through the touch pad 122, the location of the cursor seen on monitor 120. The eye to be imaged is chosen and the session is started by activating the start icon with the cursor.

A voice message instructed the subject in the use of the camera. Following the instructions, the subject leans on nose pad 112 thereby activating switch 114 that verifies proper positioning. The subject identifies the patient button and depresses it for practice.

The voice continues to instruct the subject to look at a light (one of diodes 176 and 178) and to press the button 118 when it is seen flashing. Prior to the fixation light the pupil is automatically centered and focused.

That is, as shown in FIGS. 3 and 4, the optical head or subsystem 102 further includes diodes 184 which illuminate the iris of the eye 154 with infrared light. The infrared light scattered by the pupil is reflected by infrared mirror 182 and front surface mirror 180 and is projected by lens 186 on a video camera 188. The infrared reflecting mirror 182 transmits visible light and prevents infrared light from reaching the fundus imaging optics (e.g., lenses 160 and 162 and video cameras 166). The use of infrared light permits the optical head to image the pupil without constricting it and without the subject noticing it. The output of camera 188 is fed into an image acquisition board located in computer 116.

The pupil is imaged by camera 188, and even when the pupil is not in focus it appears as a disc darker than the surrounding iris, sclera and lids. The image is digitized by a board placed in the computer 116. A software algorithm thresholds the image, namely, converts the grayscale into a black and white image. The threshold is preset to convert the pupil into a black disc and the surrounding tissue to white. The image is then inverted to generate a white disc for the pupil surrounded by black. The algorithm calculates, for the pupil, the mass and the center of mass components along the horizontal and vertical axes, respectively, according to the following formulas:

$X=[\Sigma(x_i*D_i)]/\Sigma(D_i)$ for the horizontal center of mass;

$X=[\Sigma(z_i*D_i)]/\Sigma(D_i)$ for the vertical center of mass; and

Mass=$\Sigma(D_i)$ for the mass.

Where $x_i$ and $z_i$ are the coordinates of pixel i with a density $D_i$ equal to 0 or 1.

The center of the coordinates is set at the center of the camera 188 and corresponds to the center of the optics. When the center of mass coincides with the center of the image the pupil is centered and aligned with the optics. At other locations, the center of mass indicates the deviation from the center. These x and z values are used by the computer 116 to generate a proportional number of pulses to the stepper motors that control the motion of the optical head along the horizontal and vertical positioning stages, respectively.

After each motion of the linear stages 104, 106 and 108 (FIG. 1), a new image is acquired and the new center of mass is calculated followed by a displacement of the pupil center of mass to the center of the image. The steps are repeated a preset number of times. If this number is exceeded, the procedure, is aborted and the linear stages are brought to their default position. Prior to using a given image to move the stages, a quality check is performed on the image.

That is, in order to verify that the subject is looking at the correct fixation light the images of the iris with the reflections of the illuminating diodes 184 are analyzed. Because the pupil is well centered, the location of the reflections relative to the center of the pupil is specific to each direction of gaze necessary to fixate at a given target. The reflections are identified by object recognition known in the art and their location is compared to the expected one stored in a table.

Once the unfocused pupil has been brought to the center of the image, a series of 7 images are digitized in 210 msec while the Y linear stage is moved toward the eye from a default location. For each of the seven images, a density profile is obtained along an horizontal line passing close to the center of the pupil and away from the reflections from the illuminating light emitting diodes 184. The derivative of the density profile is calculated and the maximum and minimum are recorded. Seven values are obtained for the maxima and seven for the minima. The algorithm identifies the image for which the absolute values reach their highest value. This image is the best focused one. If the maxima and minima reach their highest absolute value at frames m and n, (m+n)/2 is taken as the location of the best focus. The identification of the most focused image is translated into displacement of the linear stage and the stage is brought to that location. If necessary, the procedure can be repeated across a narrower range of motion centered on the previous location of rough focus thereby refining the focus.

Alternatively, the most focused image of the pupil can be determined based on calculating the "mass" of the white image representative of the pupil. That is, as described above, when the image is digitized and a threshold is applied, the pupil is represented by white pixels, while the area surrounding the pupil is represented by black pixels. If the pupil is out of focus, a region of gray pixels will be present between the white pixels (the pupil) and the black pixels (the area surrounding the pupil). Some of these gray pixels will be converted to black. However, once the pupil becomes in focus, the amount of gray pixels contributed by the pupil will decrease and thus, the amount of white pixels will increase. Hence, when the apparatus determines that the maximum amount of white pixels are present in the image, the apparatus concludes that the pupil is in optimal focus.

If the quality check described above is not passed the procedure is repeated a preset number of times after which the procedure is interrupted and the operator is prompted to identify the reason for the obstruction of the pupil or the lack of response of the subject. During the centering and focusing of the pupil the patient views the light and is free to blink. The procedure takes less than 1 second.

Upon correct centering and focusing of the pupil, the fixation light is flashed and the subject presses on the button. This causes the fundus focusing procedure to take place. This procedure takes less than ½ seconds. If the subject does not respond within a preset time delay the voice provides further instructions and the procedure is repeated.

Once the pupil is centered and in focus, the fundus is automatically focused. This is achieved by presenting the subject with a fixation light so that the region next to the optic disk is imaged. This area is chosen as it always contains large and small blood vessels. The shutter is turned on (i.e., blade 142 is moved to allow light from bulb 130 to pass) for 240 msec or about 240 msec and eight frames (i.e., about 30 msec per frame) are digitized by camera 166 while motor 174 moves lens 162 across a large range. For each of the eight frames, a region of interest that crosses some large and small vessels is selected. On each of these regions, a frequency transform such as a Fast Fourier Transform is performed, yielding a two dimensional array in the frequency domain. The components in a predetermined region of this domain are summed and eight values are obtained.

The frame with the maximal sum is identified and the corresponding location of lens 162 is derived. The motor is moved to that location where lens 162 provides the most focused image. If necessary the procedure can be repeated across a narrower range of motion centered on the previous location of rough focus thereby refining the focus.

The images acquired during the fundus focusing procedure are also used to determine the illumination level. The average pixel density is calculated and compared to the desired range (for example 80 to 120 for a 256 (or 8 bit) gray level image). The deviation from the desired range is used to change the light output of the bulb (1). In one embodiment, this is achieved by adjusting the duty cycle of the alternating voltage supplied to the bulb 130.

Once the fundus is focused and the light is adjusted, the plurality of targets 176 and 178 corresponding to the different areas in the fundus are presented in sequence. For each desired location on the fundus, a single diode is turned on. For each location, the image of the pupil is tracked, centered and focused. The shutter containing blade 142 is opened for the time necessary to digitize, at video rate, up to 8 images. During the procedure the subject is provided with voice feedback and instructions if quality tests are not passed.

The fundus image acquisition can be performed in a variety of modes. Two such modes are described herein. In each of these modes, the shutter controlling blade 142 is turned on for 120 msec or about 120 msec during which four frames are digitized. In the first mode, the four frames are acquired while lens 162 is moved in a range around the fine focus. This mode ensures that the most focused image is always acquired even if the refractive error changes for the particular gaze corresponding to the fixation light. This could occur if the retina is not at the same distance from the lens or in the presence of marked variations in local corneal power.

In the second mode, the four frames are acquired while the optic head 102 is moved in the x-axis (perpendicular to the optical axis). This mode permits to acquire images through four well-defined locations across the pupil.

A pair of images obtained from two opposite horizontal locations in the pupil generates a stereo image. The pair with the larger separation yields a better stereo base and thus a better stereoscopic effect. The pair with the smaller separation ensures that some stereopsis can be obtained even in the presence of illdilated pupils. This mode has the additional advantage in the presence of anterior segment opacities. If a local opacity deteriorates the image of the fundus, the acquisition of multiple images through different locations in the pupil enhances the likelihood to obtain a useful fundus image.

After each fundus image acquisition, a quality control algorithm is applied. A variety of checks can be applied and one embodiment is described. When the pupil is well centered and not obstructed by the lids, the image of the fundus is good (once it has been focused by the algorithm above). Thus an algorithm checks the mass of the pupil (after the threshold procedure mentioned above) and compares it to the minimum pupil mass required. In addition, the mass of the central 5 mm portion of the pupil is checked and required to be close to that of a 5 mm disc. These checks are efficient in detecting blinks and obstructions by the lashes. The quality of the pupil focus can also be checked by comparing the maximal derivative (or more) to that obtained during the fine pupil focusing mentioned above.

After images have been acquired at all locations the operator is presented with the images on the monitor and given the choice to repeat some of the images if deemed necessary. This is achieved by pointing the cursor to the desired image and clicking on it.

The voice prompts the operator to decide whether to image the other eye and, if so, the procedure is repeated.

At the end of the acquisition, the subject is informed of completion. All the images are stored in the computer along with a log documenting the operations that took place during the session. The data representative of the images stored in the computer can then be transmitted to another location, for example, an image reading center. At the image reading center, the images of the different locations on the fundus are automatically arranged to create a mosaic image of the entire imaged area of the fundus. For example, it images have been taken of nine different areas of the fundus (3×3 fundus images), then these nine images will be arranged to create a single image of this entire imaged area of the fundus. This arranging of the fundus images into the mosaic image can alternatively be performed by the computer 116, if desired, and data representing the mosaic image can be transmitted to the image reading center.

It is further noted that once the image of the fundus has been properly focused on camera 166, the plane 164 is conjugated to the fundus. Objects placed at this plane are imaged on the fundus under best optical conditions. The optical conditions are optimized by the focusing and by the nature of the optics of the optical head. As mentioned, the aperture 148 of mirror 146 is conjugated to the cornea of the subject and its size is small. The imaging thus depends only on the central 2 or 3 mm of the cornea. Because of the small size of the effective aperture on the cornea, only the cylindrical power of the central cornea practically affects its optical quality. Deviations from the power needed for optimal imaging are thus corrected by the placement of lens 162. In other words, the imaging does not depend on the peripheral cornea that may have local variation in optical power (astigmatism). The advantage of imaging under these conditions is well known in the trade.

Under these conditions, the quality of the image obtained by the screening camera directly reflects the optical conditions of the eye under examination. This image can then be utilized by the eye care specialist to determine if the psychophysical response has been influenced by the optics. Moreover, the sharpness of the image can be measured by a plurality of means such as analysis in the frequency domain mentioned above.

The automatic centering and axial positioning of the optical head relative to the pupil also has assured that the imaging path is at the center of the pupil. The imaging of the pupil by camera 188 and the optics prior to it, also permits the objective determination of the size of the pupil. Only eyes with a pupil size that does not interfere with the imaging path are to be considered for psychophysical tests.

As mentioned, for each target presented to the patient, a corresponding unique area on the fundus is imaged. Moreover, as mentioned, for each such area on the fundus, there is a unique pattern of reflection on the cornea once the pupil is centered and in focus. By presenting fixation targets to the subject and monitoring the reflection on the cornea one can determine the area of the fundus conjugated to is plane 164. Therefore, an object placed at location 164 is projected on a known location on the fundus thereby establishing an objective, documented relationship between the origin of the psychophysical response (or lack of it) and anatomy.

Therefore, after the imaging of the fundus has been performed, a plurality of psychophysical tests can then be performed, namely, a visual acuity test and a perimetry (visual field) test. Other psychophysical tests, such as color recognition, contrast recognition, and so on, can also be performed. As shown in FIG. 4, to perform a visual acuity test, camera 166 is replaced with assembly 190 by rotating plate 192 with motor 194. Assembly 190 comprises a light source 196 and a screen 198. Letter or graphic objects printed on screen 198 are projected on the fundus and the subject is asked to identify or detect them in a manner similar to a vision chart. Each correct response is entered by the operator into the computer with the use of touch pad 122 and screen 120 (FIGS. 1 and 2).

Pluralities of peripheral visual tests can be performed by modifying assembly 190. A screen such as a back lit monitor can replace light source 196 and screen 198. The computer can present pluralities of graphical objects. One such object consists of a grating varying in local and temporal contrast. While the subject is fixating on one of the diodes 176, the grating is turned on and off and the subject is asked to respond via button 118 (FIGS. 1 and 2). In such a manner a map of the visual sensitivity is generated similarly to perimetry.

It is noted that the psychophysical tests, in particular, the perimetry (visual field) test are performed after the images of the fundus have been obtained. In this event, the map of the visual sensitivity can be correlated with the areas of the fundus. That is, as a subject is fixating on one of the diodes 176, the portion of the fundus that was imaged when the subject was fixating on that diode is the portion of the fundus sensing the stimulus is known. Therefore, if the subject has difficulty in sensing the stimulus while fixating on that diode, it can be ascertained is that that portion of the fundus and possibly its corresponding visual pathway may have a physical abnormality.

After the above tests and fundus imaging have been performed, the results of the test and the images can be transmitted to a remote location. That is, at night, the computer connects to a communication network like the Internet and automatically transfers the data to a server located in the reading center. During the next connection the reading center server provides acknowledgment of receipt and the files are deleted from the computer in the optical head. The communication also allows the reading center to activate periodic diagnostic tests of the optical head to verify its proper operation and identify the need for service.

At the reading center the images are archived and managed through a workflow. Pluralities of operations are performed. For example, quality tests are performed on the images and the best image is chosen for each location on the fundus. The images are presented as a raster or one by one to a reader expert in detecting the necessary pathology. As described above, the fundus images are arranged into a mosaic image of the fundus. Also, the response to the visual acuity test is analyzed by a computer and the visual acuity is determined following the manner used in the trade.

The analysis of the responses to the visual field test is performed. The images of the cornea and iris are used by an algorithm to determine the location of the reflections on the cornea relative to the center of the pupil. This location is compared to that obtained during imaging and the location of the stimulus on the fundus is determined. A fundus map of the responses is generated. The quality of the fixation by the subject is assessed. If a sufficient area of the fundus was covered, statistical calculations used in the trade of perimetry are performed to determine whether the visual field is normal or not. If the coverage is not adequate but at least one of the responses is found abnormal, the test can be considered positive thereby justifying referral to an eye care specialist.

The results are computerized and a report is issued to the health care professional.

Figure 5:
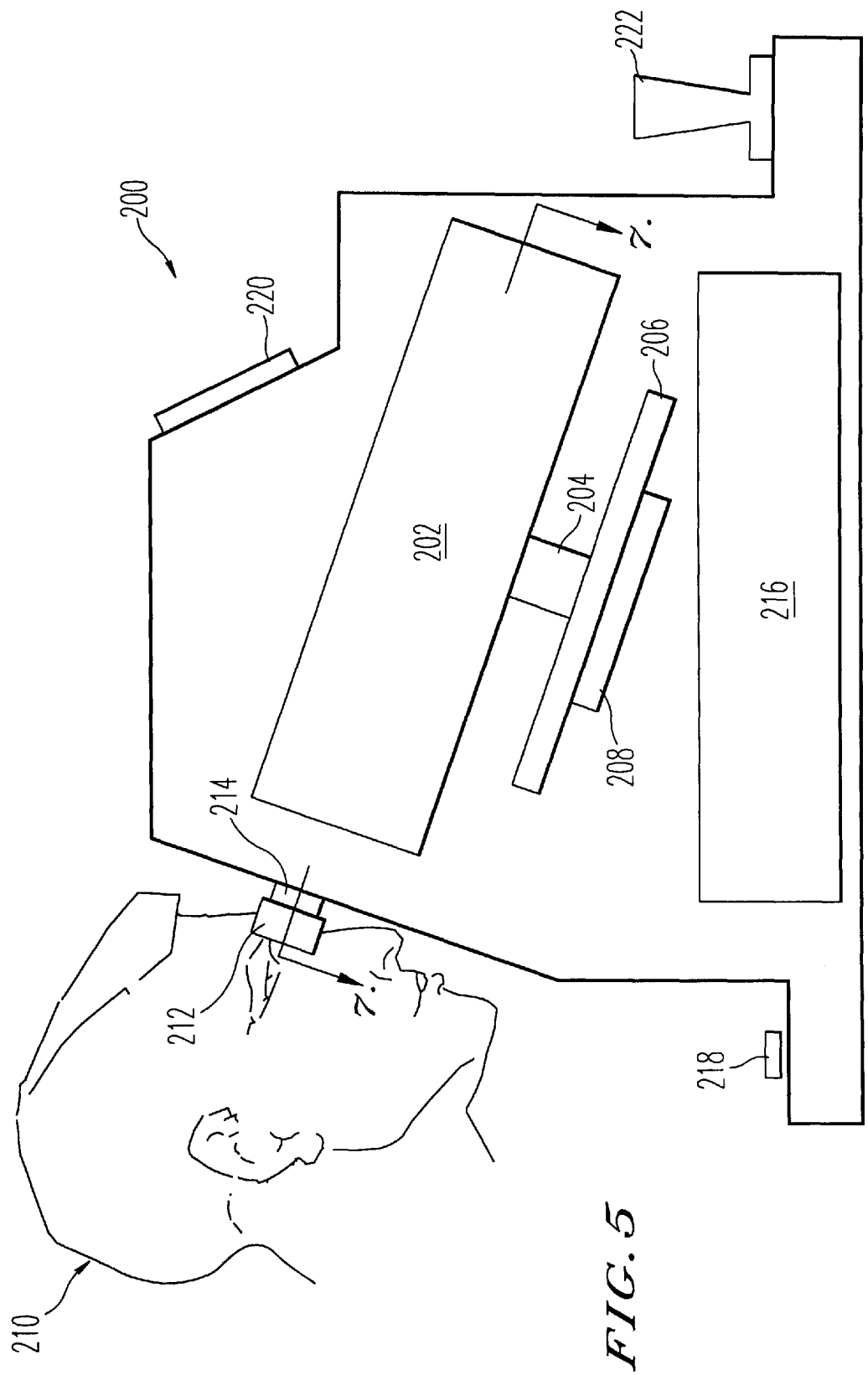
FIG. 5 is a schematic view of an imaging system according to a second embodiment of the invention, which is employed as a data acquisition system for obtaining an image to be transmitted to a remote data reading center.

A system according to another embodiment of the invention is shown in FIGS. 5–8. Specifically, FIG. 5 is a schematic illustrating an example of an imaging system 200 similar to imaging system 100 described above. The system includes an imaging head or subassembly 202 which is mounted on an XYZ motorized and computer-controlled stage comprising components 204, 206 and 208. The components 204, 206 and 208 are responsible for movement in the X, Y, and Z directions, respectively, During operation, the subject 210 leans against one of two nose pads 212 (one for imaging each eye) and views the target diodes (see FIGS. 7 and 8) inside the imaging subsystem 202 used for fixation. A switch 214 provides a signal to computer 216 indicating the presence of the nose at a nose pad 212.

The electronics and computer 216 that control the entire system are placed under the imaging sub-assembly. The subject is provided with a button 218 and the operator is provided with a monitor 220 and a joystick control,222. The use of these two latter items is described below.

Figure 6:
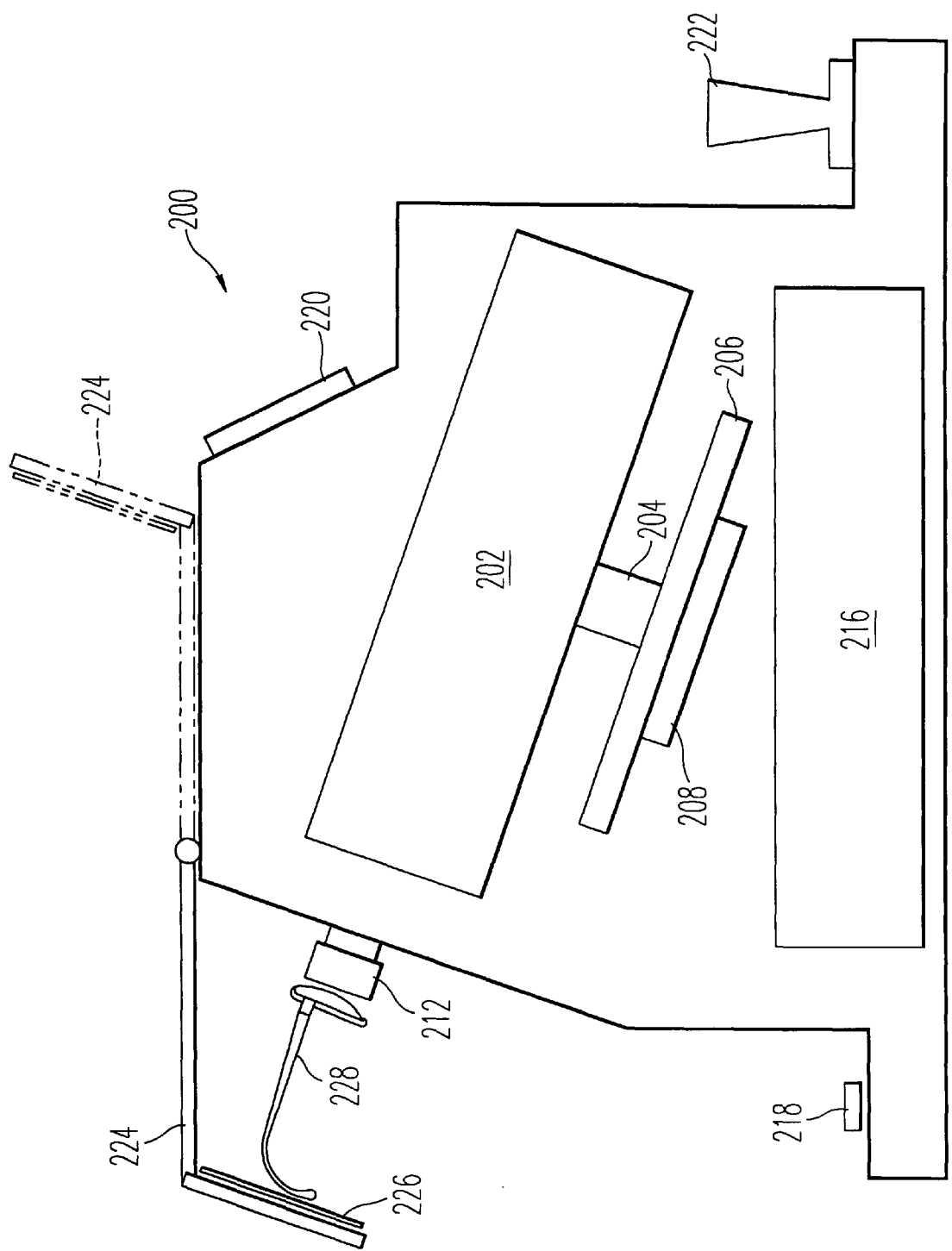
FIG. 6 is a schematic view of the imaging system as shown in FIG. 5 for performing a refractive error estimation procedure.

As shown in FIG. 6, a holder 224 is able to flip from a resting position (shown by dotted lines) to a preset distance from the nose pad 212. The subject's chart 226 or any other standardized identification sheet, is placed on an inner surface of the holder 224 when the holder 224 is at the preset distance from nose pad 212. To estimate the subject's refractive error and to set the initial position of a focusing lens (see FIGS. 7 and 8) for a particular eye, the subject's spectacles 228 are held by a spectacle holder (not shown) in front of the camera in the manner shown. The instrument performs the focusing routine mentioned above and determines the location of the lens needed to focus the image of the chart 226. This position of the lens is stored by the computer 216 and taken into account when automatic focusing of the fundus image is later accomplished.

After estimation of the refractive error, the holder 224 is reset to its storage position and the subject leans against the instrument and contacts one of the nose pads 212 and 213 (FIG. 7) with the bridge of the nose. To ensure that the subject does not move away. The microswitch 214 is placed under the nose pad provides a signal to computer 216 if pressure is relieved and the switch opens. In this event, the fixation target is turned off, and a warning audible signal is generated.

Figure 7:
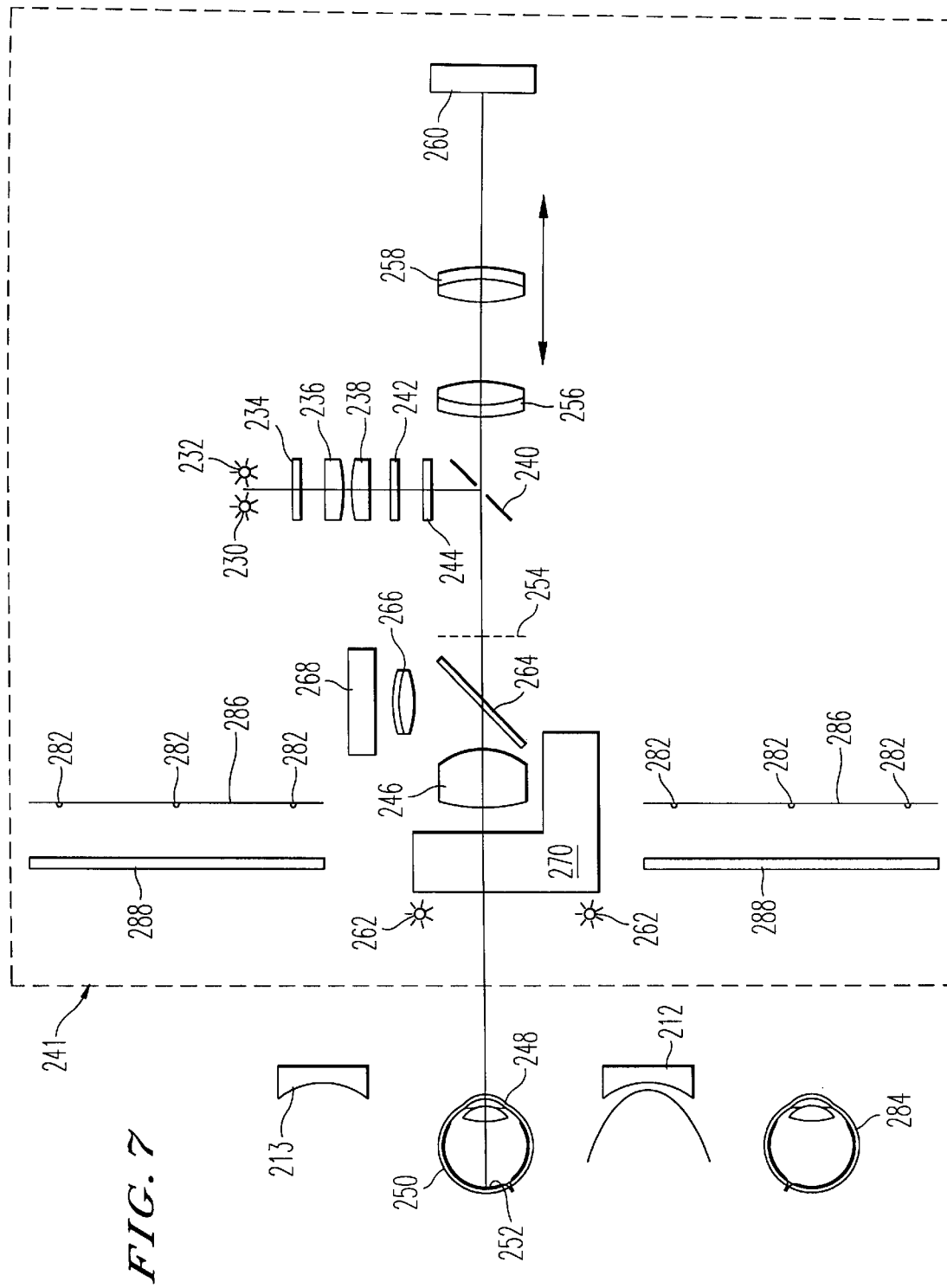
FIG. 7 is a schematic inverted cross-sectional view of the system shown in FIG. 5 as taken along lines 7—7 in FIG. 5 and illustrating, in particular, the optical head.
Figure 8:
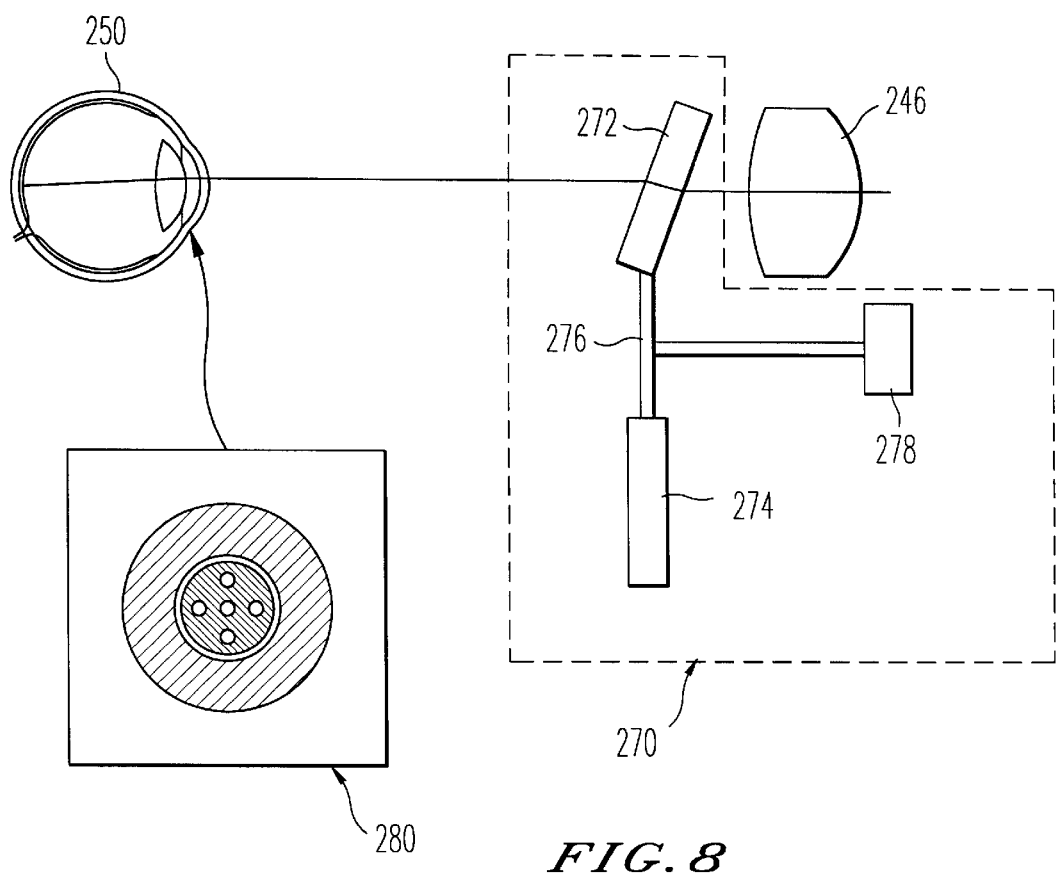
FIG. 8 is a schematic inverted cross-sectional view of the system shown in FIG. 5 as taken in a direction perpendicular to lines 7—7 in FIG. 5 and illustrating, in particular, the optical head, and further including an insert illustrating five positions of the pupil through which images are taken.

An example of the fundus imaging head or subsystem 202 in accordance with this embodiment of the present invention is shown schematically in FIGS. 7 and 8. The fundus imaging head or subsystem 202 includes two halogen bulbs 230 and 232. The bulbs 230 and 231 generate light from which infrared light is eliminated by a filter 234. The beams are collimated by tens 236 and focused by lens 238 on a mirror 240. The beams are filtered by filter 242 to yield green light (around 540 nm). A computer controlled shutter 244 turns the light beams on and off. The light from bulbs 230 and 232 is reflected by mirror 240, and the light bulb filaments are imaged by lens 246 on the pupil 248 of the eye 250. Thus, the filaments of the two bulbs are imaged on the pupil at two corresponding spaced locations at the 3 and 9 clock hour positions on the pupil. From the pupil, the beams expand and illuminate the fundus 252.

The image of the fundus 252 is created on a conjugate plane 254. Lenses 256 and 258 work together to transfer the image at the conjugate plane 254 to the sensing area of a video camera 260. Lens 258 is moved to compensate for the spherical refractive error of the eye and thus to optimize the focus on the sensing area of video camera 240. The motion of focusing lens 258 is achieved by mounting it on a conventional linear bearing assembly (not shown) and positioning it by a computer controlled linear actuator.

Diodes 262 illuminate the iris of the eye with infrared light. The infrared light scattered by of the pupil is gathered by lens 246, reflected by an infrared mirror 264 and projected by lens 266 to provide an image to a video camera 268. The infrared reflecting mirror 264 transmits visible light and prevents infrared light from reaching the fundus imaging optics (e.g., lenses 256, 258 and video camera 260).

FIG. 8 illustrates in greater detail the pupil scanning assembly 270 of FIG. 7. In FIG. 8, it can be seen that different glass plates such as 272 and 274 are arranged with various tilts on a mounting disc 276. By rotating the disc 276 with a motor 278 so as to place the various plates of different tilts in front of the optics, the incoming illumination beams can enter the pupil from different locations and provide corresponding reflected fundus imaging paths in the pupil. The insert 280 in FIG. 8 illustrates a preferred arrangement of five locations on the pupil achieved by five different plates.

The acquisition of a plurality (preferably five) of images through a plurality (preferably five) of corresponding different locations in the pupil mimics the procedure used by a trained observer to obtain a clear image in the presence of local opacities in the lens of the eye. The present invention thus ensures that a clear image can be automatically acquired in the presence of local opacities in one or more locations without the need for a trained observer.

Stereophotographs are obtained by acquiring images at the two horizontal locations corresponding to clock hours 3 and 9 in the pupil (FIG. 8). These two images can be acquired at consecutive video frames, that is, within 60 msec. The stereo base is constant and determined by the tilt of the glass plates used in the pupil scanning assembly 270.

The gross alignment of the eye is performed by the operator. The image of the pupil generated by camera 268 is viewed by the operator on monitor 220. The operator activates the joystick 222 to move the imaging subassembly 202 in the XYZ directions relative to the eye, until the pupil image is close to the center of the monitor 220. The imaging subassembly 202 is also moved axially until the pupil is generally focused and visible on the monitor. At this point, a computer algorithm processes the image of the pupil and determines the center of the pupil image. The computer then determines the deviation of the pupil image from the center of the monitor 220. The deviation is used by the computer to drive the XYZ table automatically to null this deviation. Pupil tracking is performed at video rate and the alignment is performed at 15 Hz or more. As a result, the pupil image is automatically centered on the display 220 in less than a second.

To obtain images at different locations on the fundus, the eye is directed to different orientations by presenting a plurality of light emitting diode targets 282 for the fellow eye 284 (i.e., the eye opposite to that being imaged) to follow. In the great majority of cases, the eye being imaged will move in substantially the same fashion and to the same orientation as the fellow eye. Although it is contemplated that the targets may be presented and viewed by the eye being imaged, use of the fellow eye as aforesaid is preferred. As shown in FIG. 7, fellow eye 284 views the light from one of the light emitting diodes 282 arranged in a raster on plate 286. The diodes are brought into focus by a Fresnel lens 288. It is preferred that an array of nine (3×3), twelve (3×4) or sixteen (4×4) diode targets 282 be used for each eye. In FIG. 7, an array of (3×3) diodes are used (only 3 diodes are shown for each eye in FIG. 7).

To acquire an image of the fundus, the output of video camera 260 in FIG. 7 is digitized by an image digitizing board activated by a computer 216 (see FIG. 5) in synchronization with a video triggering signal. The triggering signal is produced by the output from camera 260 or timing electronics in the computer 216. Each digitized image is first stored in the computer RAM and later transferred to storage medium (e.g. hard drive).

For each eye to be imaged, an optimal focus of the image is achieved by obtaining a series of images (fields at video rate –approximately 60 fields/second—for a total time of 130 msec) through a central one of the five locations of the pupil (see insert 280 of FIG. 8). For each of the images (preferably, eight images are taken), the focusing lens 258 is displaced by a predetermined distance in synchronization with the video camera 260. The eight images stored in RAM memory are examined by a computer algorithm to identify the image with the best focus. The location of lens 258 used to obtain this image is stored and used for later focusing.

The manner in which the images of the fundus are taken is as follows.

The major refractive errors are set by the instrument following the measurement obtained with the spectacles. The first target is then presented to the subject. When the first target is viewed by the subject, the subject's eye is oriented to enable a fundus image of the upper arcade of retinal vessels to be recorded by the video camera 260. The use of this target ensures that the image includes blood vessels, objects with contrast and details, thus making focusing optimally reliable.

As soon as pupil image centering is achieved, illumination is effected by opening shutter 244. The aforementioned series of eight images (fields) is acquired at video rate, each at a different position of the focusing lens 258, and the illumination is then terminated by a closing shutter 244. The position of lens 258 for the best focus is saved by the computer.

The plurality of different targets 282 corresponding to the different areas in the fundus are presented in sequence. For each desired location on the fundus, a single diode 282 is turned on. For each location, the image of the pupil is tracked and centered on the monitor 220 as mentioned above. Once the pupil image is centered as detected by the computer 216, the computer generates a signal so that a speaker generates a beep to attract the attention of the patient and thereby request the patient to depress button 218 when he detects that the target diode 282 begins flickering. The flickering begins shortly after the beep. The delay between the flickering onset and the subject's response is measured and the computer software routine assesses if it is shorter than a preset standard time. This process is used to ensure that the subject fixates well on the target. If the delay of the response is short enough, a series of five images of a particular location on the fundus corresponding to the particular target 282 is immediately acquired in less than 250 msec, which is the time delay for a voluntary eye motion. Each of these five images is acquired through a different location in the pupil with the use of the pupil scanning protocol mentioned above. The five digitized images are analyzed by the quality control software algorithm. The optimal one out of the five is identified, and the corresponding location in the pupil is recorded. The image can be presented to the operator via display 220 to enable the operator to decide to accept it or repeat the acquisition through input via the joystick. Acceptable images are saved.

The next target is presented and the acquisition is repeated. It is possible to limit the acquisition to less than 5 images by acquiring images through the region in the pupil previously identified as optimal. When stereo imaging is necessary, the images acquired at the 3 and 9 o'clock hour positions are saved.

Computer software routines are designed to assess the, quality of focusing and of exposure. These quality controls allow the identification of the optimal image within a series of images and provide an indication if a blink or motion of the eye occurred during data acquisition. Should such blinking or motion occur, the fixation target 282 for which data was being taken is presented again.

To image the other eye, the subject leans the nose bridge on the other pad 213 and the above procedures are repeated.

At night, the computer at a remote reading center connects, via a phone line, to the computer 216 which is set in a 'slave' mode. Thus, the computer at the reading center can upload new data, reset parameters, erase previous files as well as download updated software.

The reading center is equipped with multichannel communication hardware and software to receive and store images from multiple optical heads at different or the same facility.

The data is decompressed and processed. A computer software routine creates a mosaic of 3×3 or 4×4 images for the aforementioned preferred total of 9–16 image corresponding to the different targets. The mosaic is first based on the location of the target used for each image. A fine adjustment is then performed based on the auto-correlation between the overlapping areas in the adjacent images. Alternatively, the computer 216 can create the mosaic image and upload data representing that image to the reading center.

Basic images enhancements, such as contrast enhancement and intensity equalization, are applied. The images are then stored along with the patient data.

A reader scrolls through the composite image and the data files. The images are displayed on a large, high resolution monitor and the reader marks the different pathologies with a pointing device. The location and nature of the pathology are automatically recorded in a file. A grading algorithm analyzes the data according to clinical standards such as those of the ETDRS, determines the degree of retinopathy and presents the recommendation to the reader. The grading and the recommendation are reviewed by the reader and, once accepted or modified, the information is stored. A report is issued to the primary care physician and other legal parties as determine the user.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. An ophthalmic imaging system comprising:
    an image obtaining device, adaptable to automatically obtain images of different locations on the fundus of an eye; and
    an image arranging device, adaptable to automatically arrange the images of the different locations of the fundus into an image representative of an area of the fundus comprising the different locations.

2. An ophthalmic imaging system as claimed in claim 1, wherein:
    the imaging obtaining device obtains the images which each have a field of view of less than or equal to 30° as measured as a conical angle originating at the pupil of the eye and extending toward a corresponding location on the fundus being imaged.

3. An ophthalmic imaging system as claimed in claim 1, wherein:
    the image arranging device arranges the images of the different locations of the fundus into the image representative of the area of the fundus comprising the different locations such that the representative image has a field of view of equal to or greater than 50° as measured as a conical angle originating at the pupil of the eye and extending toward the area being imaged.

4. An ophthalmic imaging system as claimed in claim 1, wherein:
    the image obtaining device comprises:
        at least one illuminating device, adaptable to emit light onto the different locations of the fundus; and
        a light detector, adaptable to detect light reflected from the different locations of the fundus in response to the light emitted thereon by the illuminating device.

5. An ophthalmic imaging system as claimed in claim 1, wherein:
    the image obtaining device obtains two of said images for each of the different locations of the fundus; and
    the image arranging device arranges the two images of each of the different locations of the fundus such that the image representative of the area of the fundus is a stereo image.

6. An ophthalmic imaging system as claimed in claim 5, wherein:
    the image obtaining device comprises:
        an illuminating device, adaptable to emit light onto each of the different locations of the fundus; and
        a light detector, adaptable to detect light reflected from each of the different locations of the fundus in response to the light emitted thereon by the illuminating device.

7. An ophthalmic imaging system as claimed in claim 1, wherein:
    the image obtaining device comprises an electronic camera which is adaptable to automatically obtain the images of different locations on the fundus of an eye.

8. An ophthalmic imaging system as claimed in claim 7, wherein the electronic camera is a video camera.

9. An ophthalmic imaging system as claimed in claim 1, wherein:
    the image obtaining device obtains a plurality of the images for each of the different locations on the fundus of an eye.

10. An ophthalmic imaging system as claimed in claim 9, wherein:
    the image obtaining device obtains the plurality of image for said each of the different locations during a time period less than 250 milliseconds.

11. An ophthalmic imaging system as claimed in claim 1, wherein:
    the image obtaining device is adaptable to automatically focus each of the images of the different locations on the fundus of an eye.

12. An ophthalmic imaging system as claimed in claim 1, further comprising:
    an evaluating device which is adaptable to evaluate each of the images of the different location on the fundus of the eye, obtained by the image obtaining device, to determine whether each of said images meets a predetermined quality criteria.

13. An ophthalmic imaging system as claimed in claim 1, further comprising:
    a second image obtaining device, adaptable to obtain an image of the pupil of the eye.

14. An ophthalmic imaging system as claimed in claim 13, wherein:
    the second image obtaining device is adaptable to automatically focus the image of the pupil of the eye.

15. An ophthalmic imaging system as claimed in claim 13, further comprising:
    an evaluating device which is adaptable to evaluate the image of the pupil of the eye, obtained by the second image obtaining device, to determine whether the image of the pupil meets a predetermined quality criteria.

16. An ophthalmic imaging system as claimed in claim 15, wherein:
    the second image obtaining device is adaptable for obtaining a plurality of images of the pupil of the eye; and
    the evaluating device is adaptable to distinguish those of said images of the pupil of the eye that were obstructed by a lid of the eye from those of said images of the pupil of the eye unobstructed by a lid of the eye.

17. An ophthalmic imaging system as claimed in claim 13, further comprising:
    an adjusting device, adaptable to adjust a location of the image obtaining device relative to the eye based on the image of the pupil obtained by the second image obtaining device.

18. An ophthalmic imaging system as claimed in claim 13, wherein:
    the second image obtaining device comprises:
        at least one light emitting device, adaptable to emit light onto the iris of the eye; and a light detecting device, adaptable to detect light reflected from the iris in response to the light emitted thereon by the at least one light emitting device.

19. An ophthalmic imaging system as claimed in claim 18, wherein:

the at least one light emitting device is an infrared light emitting device.

20. An ophthalmic imaging system as claimed in claim 18, wherein:

the at least one light emitting device is adaptable to emit light onto different locations of the iris of the eye; and the light detecting device is adaptable to detect light reflected from the different location of the iris in response to the light emitted thereon by the at least one light emitting device.

21. An ophthalmic imaging system as claimed in claim 1, further comprising:

a vision evaluating device, adaptable to perform at least one physchophysical test on the eye at different locations on the fundus of the eye after their images have been obtained.

22. An ophthalmic imaging system as claimed in claim 21, wherein:

the vision evaluating device evaluates field of vision of the eye as one of the physchophysical tests.

23. An ophthalmic imaging system as claimed in claim 1, further comprising:

a data transmitter, adaptable to transmit data representative of the images of different locations on the fundus of the eye to the image arranging device, which is at a location remote from the image obtaining device.

24. An ophthalmic imaging apparatus comprising:

at least one light emitting device, adaptable to emit light onto at least one location on the iris of the eye;

a light detecting device, adaptable to detect light reflected from the iris in response to the light emitted thereon by the at least one light emitting device; and an image obtaining device, adaptable to automatically focus and center the image of the pupil of the eye to form an image of the pupil of the eye based on the light detected by the light detecting device.

25. An ophthalmic imaging apparatus as claimed in claim 24, further comprising:

an evaluating device which is adaptable to evaluate the image of the pupil of the eye, obtained by the image obtaining device, to determine whether the image of the pupil meets a predetermined quality criteria.

26. An ophthalmic imaging apparatus as claimed in claim 24, wherein:

the image obtaining device is adaptable for obtaining a plurality of images of the pupil of the eye; and the evaluating device is adaptable to distinguish those of said images of the pupil of the eye that were obstructed by a lid of the eye from those of said images of the pupil of the eye unobstructed by a lid of the eye.

27. An ophthalmic imaging apparatus as claimed in claim 24, wherein:

the at least one light emitting device is an infrared light emitting device.

28. An ophthalmic imaging apparatus as claimed in claim 24, wherein:

the at least one light emitting device is adaptable to emit light onto different locations of the iris of the eye; and the light detecting device is adaptable to detect light reflected from the different location of the iris in response to the light emitted thereon by the at least one light emitting device.

29. An ophthalmic imaging system comprising:

an image obtaining device, adaptable to automatically obtain images of different locations on the fundus of an eye; and at least one of the following:

an alignment device, adaptable to automatically align the image obtaining device with respect to the eye to enable the image obtaining device to obtain the images of any location on the fundus of the eye;

a focusing device, adaptable to automatically focus the image obtaining device with respect to the fundus of the eye to enable the image obtaining device to obtain focused images of any location on the fundus of the eye;

a transmitting device, adaptable to transmit to a remote location data representative of the images obtained by the image obtaining device;

a testing device, adaptable to perform at least one psychophysical test on the eye at different locations of the fundus of the eye after their images have been obtained by the image obtaining device; and a stereo image generating device, adaptable to generate a stereo image of any of said locations on the fundus of the eye based on the images of said any location obtained by the image obtaining device.

30. An ophthalmic imaging system as claimed in claim 29, comprising all of said alignment, focusing, transmitting, testing and stereo image generating devices.

31. An ophthalmic imaging system as claimed in claim 29, wherein:

the testing device includes a stimuli generating device, adaptable to provide optical stimuli which are registered onto the locations on the fundus whose images have been obtained by the image obtaining device.

32. A method for obtaining an ophthalmic image, comprising the steps of:

automatically obtaining images of different locations on the fundus of an eye; and automatically arranging the images of the different locations on the fundus into an image representative of an area of the fundus comprising the different locations.

33. A method for obtaining an ophthalmic image, comprising the steps of:

emitting light onto at least one location on the iris of the eye;

detecting light reflected from the iris in response to the light emitted thereon by the at least one light emitting device; and automatically focusing and centering the image of the pupil of the eye to form an image of the pupil of the eye based on the light detected by the light detecting device.

34. A method for using an imaging device to obtain an ophthalmic image, comprising the steps of:

controlling the imaging device to automatically obtain images of different locations on the fundus of an eye; and at least one of the following:

automatically aligning the imaging device with respect to the eye to enable the imaging device to obtain the images of any location on the fundus of the eye;

automatically focusing the imaging device with respect to the fundus of the eye to enable the imaging device to obtain focused images of any location on the fundus of the eye;

transmitting to a remote location data representative of the images obtained by the imaging device;

performing at least one psychophysical test on the eye at different locations of the fundus of the eye after their images have been obtained by the imaging device; and generating a stereo image of any of said locations on the fundus of the eye based on the images of said any location obtained by the imaging device.

35. An ophthalmic imaging system as claimed in claim 34, comprising all of said alignment, focusing, transmitting, testing and stereo image generating steps.

* * * * *